US 11,179,488 B2

(12) United States Patent
Bernstein et al.

(10) Patent No.: US 11,179,488 B2
(45) Date of Patent: Nov. 23, 2021

(54) SANITIZER FOR ROD OR HANDLE MEMBER

(71) Applicant: SJBEE LLC, Hewlett, NY (US)

(72) Inventors: Steven J. Bernstein, Hewlett, NY (US); Leslie S. Blitz, New Hyde Park, NY (US)

(73) Assignee: SJBEE LLC, Hewlett, NY (US)

( * ) Notice: Subject to any disclaimer, the term of this patent is extended or adjusted under 35 U.S.C. 154(b) by 0 days.

(21) Appl. No.: 17/212,731

(22) Filed: Mar. 25, 2021

(65) Prior Publication Data

US 2021/0322614 A1    Oct. 21, 2021

Related U.S. Application Data

(60) Provisional application No. 63/013,079, filed on Apr. 21, 2020.

(51) Int. Cl.
*A61L 2/18* (2006.01)
*A61L 2/26* (2006.01)
*B08B 1/00* (2006.01)

(52) U.S. Cl.
CPC ............ *A61L 2/26* (2013.01); *A61L 2/18* (2013.01); *B08B 1/006* (2013.01); *B08B 1/008* (2013.01); *A61L 2202/15* (2013.01); *A61L 2202/17* (2013.01)

(58) Field of Classification Search
CPC .. A61L 2/18; A61L 2/22; B62D 39/00; B62D 5/069; B62D 5/06; B08B 1/008; B08B 9/023; A47L 25/00; A47L 13/17; B62B 5/06; B62B 5/069
See application file for complete search history.

(56) References Cited

U.S. PATENT DOCUMENTS

| 4,953,999 | A | * | 9/1990 | Rivers | .................... A47L 13/17 |
| | | | | | 15/209.1 |
| 7,611,156 | B2 | * | 11/2009 | Dunser | .................. B08B 9/023 |
| | | | | | 280/33.992 |
| 2011/0182769 | A1 | * | 7/2011 | Rich | ........................ A61L 2/18 |
| | | | | | 422/28 |
| 2016/0095948 | A1 | * | 4/2016 | Bord | ....................... A61L 2/22 |
| | | | | | 422/300 |

FOREIGN PATENT DOCUMENTS

| FR | 2864813 A1 | * | 7/2005 | ............ B08B 9/023 |
| GB | 2429634 A | * | 3/2007 | ............ B08B 9/023 |

* cited by examiner

*Primary Examiner* — Shay Karls
(74) *Attorney, Agent, or Firm* — Ostrolenk Faber LLP

(57) ABSTRACT

A sanitizer for sliding over and sanitizing an elongated member such as a shopping cart handle includes a main body including a bottom housing and a top housing selectively interlockable with each other and defining therebetween a tunnel having a cross-sectional dimension and a general shape that match a corresponding cross sectional dimension and a shape of the elongated member. The top housing has a chamber for holding therein a sanitizing fluid dispenser that is positioned to dispense a sanitizing fluid onto the elongated member. A wiping material is disposed along the tunnel in the main body, in a position and in a manner that enables wiping the sanitizing fluid onto the elongated member as the sanitizer is slid over the elongated member.

12 Claims, 5 Drawing Sheets

SANITIZER FOR ROD OR HANDLE MEMBER

CROSS-REFERENCE TO RELATED APPLICATION

The present non-provisional patent application claims the benefit of and priority to U.S. Provisional Patent Application No. 63/013,079, filed Apr. 21, 2020, the entire contents of which are incorporated herein by reference.

BACKGROUND OF THE INVENTION

The present invention is generally directed to sanitizing devices and more specifically to a sanitizing device for handles that are used sequentially by different people, often in public settings.

A main aspect of the present invention relates to shopping carts and similar product carriers, rails or handles that need to be sanitized or cleaned and disinfected. Shopping carts and other carriers are commonly provided to a customer by the retail store as a method to collect items and transport through the store. In the post COVID 19 world there became a need to provide extra disinfection protection to the consumer using these carts. Perception has become the reality for these retailers. Studies have been done over the years to expose the level of bacteria, germs and viruses that remain on cart or door handles after and between uses from consumers shipping in the stores. In an effort to protect their customers from potential health hazards posed by unsanitary shopping cart handles some retailers have begun to provide pretreated sanitized wipes which become expensive and a future logistics and disposal issue. Some retailers do not keep the wipes near the shopping cart stations which many times are in the parking lot rather than inside the store where the wipes may be housed. When it comes to refrigerator and freezer or other door handles, and handicap rails most retailers keep sanitary wipes near the front of store rather than at the point of contact where the consumer most needs them.

SUMMARY OF THE INVENTION

In general, it is an object of the present disclosure to provide improved and highly accessible and easy to use sanitizing devices for handles of, for example, shopping carts, doors and the like used at public locations such as in department stores, libraries and the like.

The device of the present disclosure is primarily used on a shopping cart handle or can be used on other handles or rails as a consumer-controlled sanitizing apparatus. It comprises a housing for a replaceable pump action sanitizing fluid reservoir mounted into the slidable plastic housing body. The main body of the design is constructed in a way that it holds a foam spacer around the entire shopping cart handle. This will ease the mount onto the shopping cart handle by conforming to the different size shopping cart handles as well as absorb the excess liquid sanitizer and feed the easy slide sanitizing fabric liner. The device is made so that there is easy assembly to snap onto the shopping cart as well as ease in replacement of the disposable sanitizer spray unit while not so easy that the consumer or a child can remove it from the cart or remove the disposable sanitizer spray unit from the housing without a special tool.

The device is built so that the main body case encircles the shopping cart handle. When the plunger is activated it will dispense sanitizing fluid on to the rail of the shopping cart along with movement of the housing body sliding along the rail. While this liquid is being disbursed, the easy slide sanitizing fabric liner is scrubbing the shopping cart rail. A back-and-forth motion across the shopping cart handle will effectively sanitize the shopping cart handrail or other door handles or handicap rails. The device contains a weight to ensure that the device always remains in the upright position on the shopping cart, while allowing the unit not to interfere with the nesting of the carts. This weight is held in place by a retainer plate which can also be used to hold an optional electronic chip to track and locate misplaced or stolen carts.

Other features and advantages of the present invention will become apparent from the following description of the invention which refers to the accompanying drawings.

DETAILED DESCRIPTION OF PREFERRED EMBODIMENTS OF THE INVENTION

Figure 8:
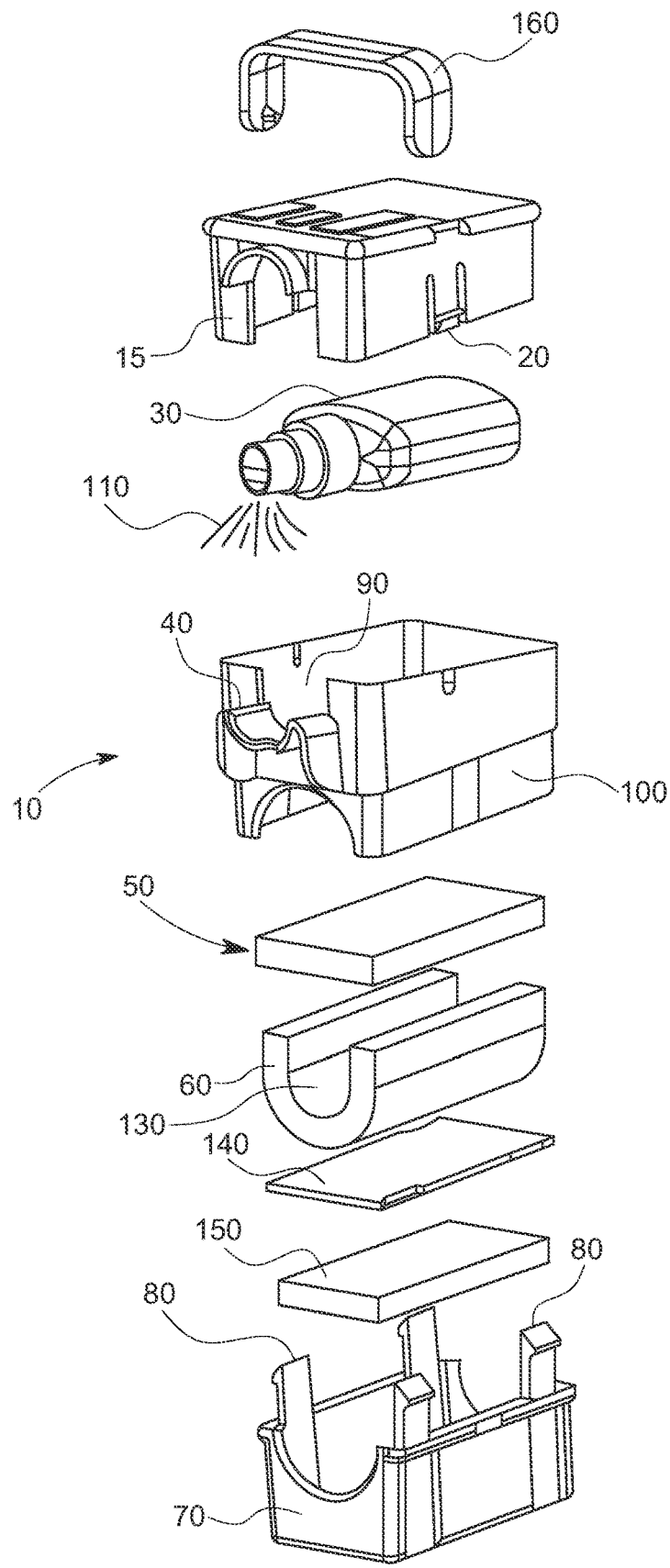
FIG. 8 is an exploded view of the components that make up Squeeze Slide and Sanitize including removal tool.

With reference to the drawings, a preferred embodiment of the invention comprises various elements that are described below, and which are identified by the "parts lists" shown below:
5 Handle or Rail
15 Top cap
20 Top Cap locking tabs
30 Disposable sanitizer spray unit
40 Main body top
50 Foam Spacer
60 Easy slide sanitizing fabric liner
70 Main body bottom
80 Bottom cap locking tabs
90 Receiving ledges for top cap locking tabs
100 Receiving ledges for bottoms cap locking tabs
110 Sanitizer pump sprayer
120 Sanitizer spray outlet
130 Space for shopping cart rail
140 Retainer plate
150 Weight
160 Removal tool With reference to the exploded view of FIG. 8, the sanitizer 10 of the present disclosure comprises a main body bottom 70 that is inter-assembled with a main body top 40, defining therebetween an interior space holding, starting from the bottom, a weight 150 that is held down by a retainer plate 150.

Figure 1:
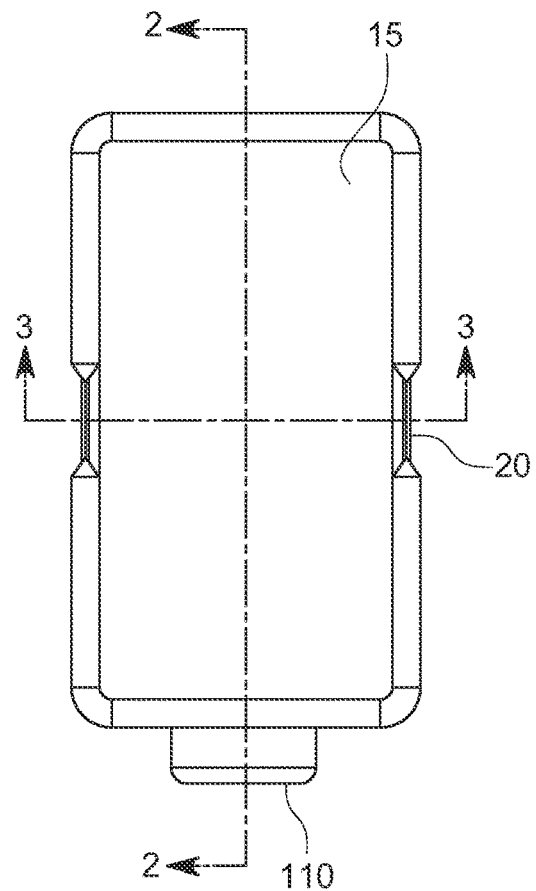
FIG. 1 is a view from the top showing the sanitizer, including a pump sanitizing fluid sprayer.
Figure 2:
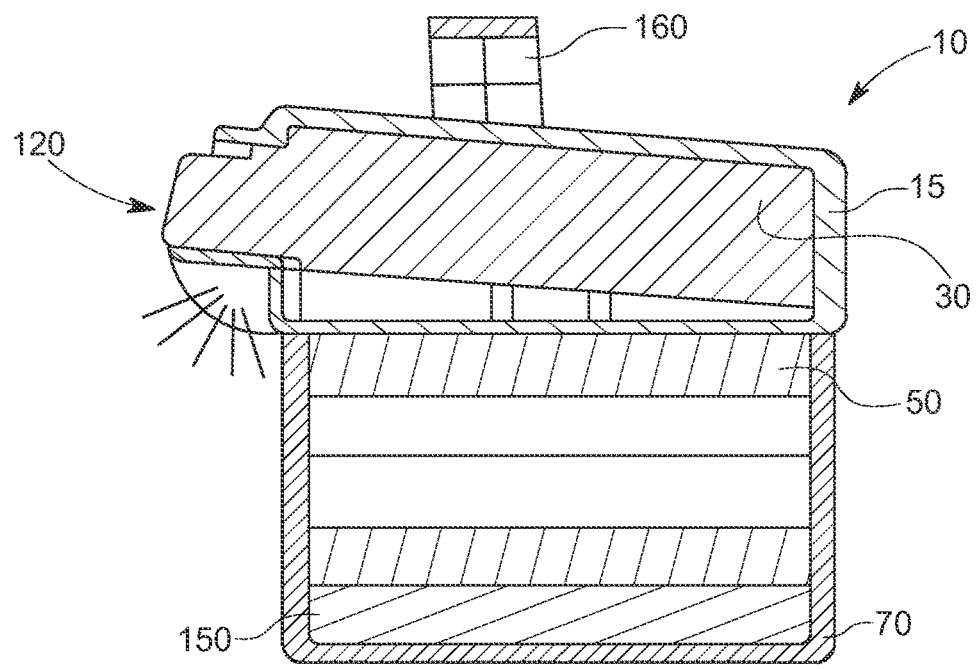
FIG. 2 is a cross section of the sanitizer taken along lines 2-2 in FIG. 1.
Figure 3:
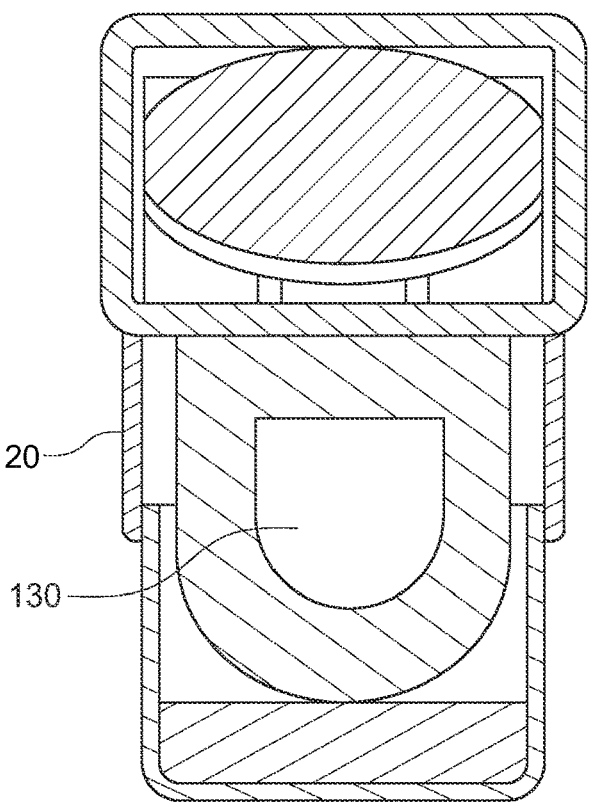
FIG. 3 is a cross section of the sanitizer taken along lines 3-3 of FIG. 1, showing the unit with the top cap mounts locked into the unit body.
Figure 4:
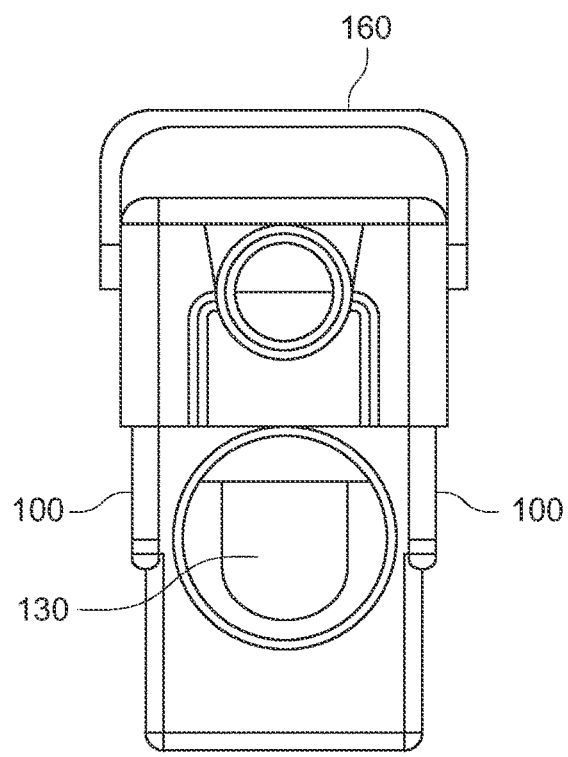
FIG. 4 is a front view of the unit showing the disposable sanitizer spray unit removal tool on top.
Figure 5:
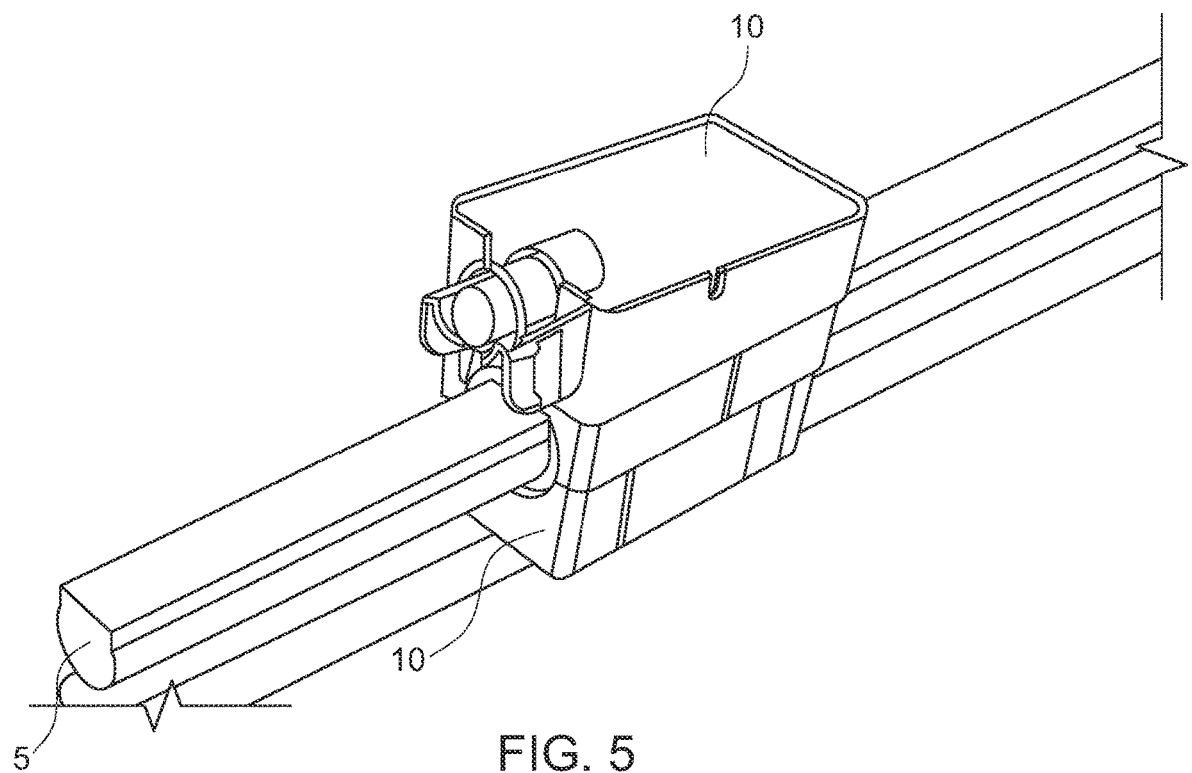
FIG. 5 is a perspective showing the device mounted upon a typical rail or handle.
Figure 6:
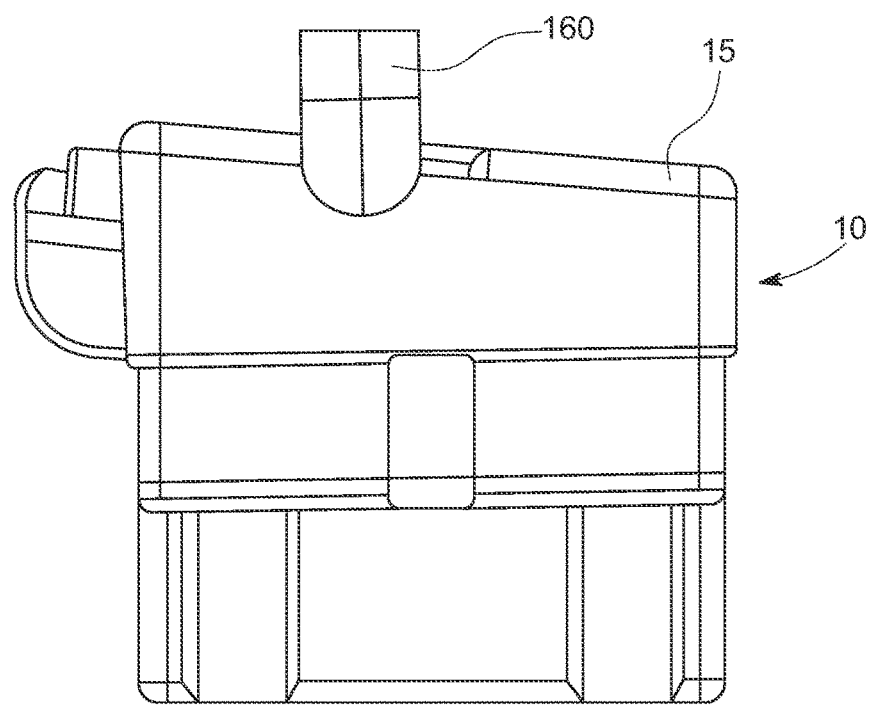
FIG. 6 is a view from the side of the unit with removal tool on top.
Figure 7:
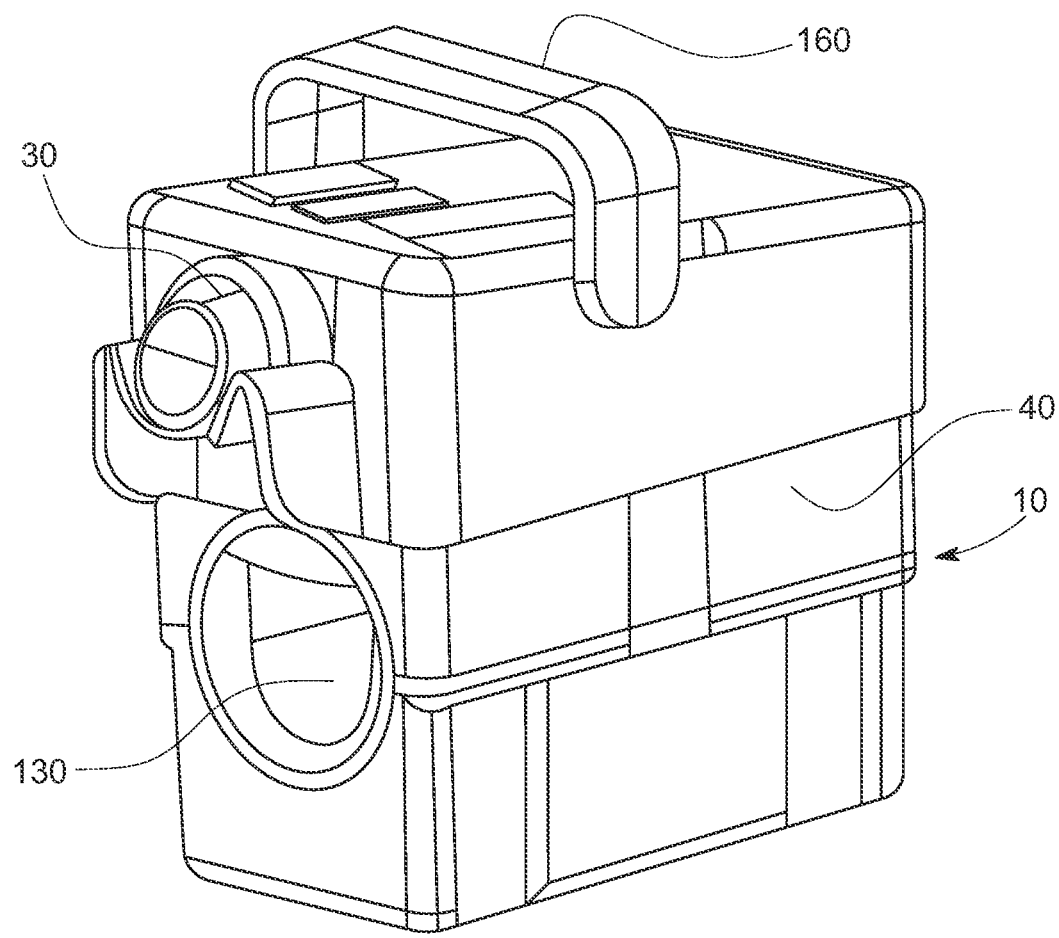
FIG. 7 is a perspective view of the entire unit assembled with removal tool on top.

The rail sanitizing components include a U-shaped liner 60 that defines a tunnel or space 130, for the holding a rail or handle 5, which space 130 is closed at the top by the foam spacer 50, allowing easy sliding of the sanitizer over the handle/rail 5 (FIG. 5). The cap locking tabs 80, preferably located at the four corners of the bottom housing 70, are configured to snap lock with the top housing 40 at the receiving ledges 100, with the rail between them.

The main body top 40 has upward extending walls that define a space for holding therein a replaceable (conventional) sanitizing fluid sprayer 30 that has a head that can be pressed in to release a spray 110, the construction being such that the spray 110 is directed at the rail 5. The replaceable sprayer 30 is retained in place by the top cap 15 during normal use, held secured to the housing component 40 via the top cap locking tabs 20 that lock to the receiving ledges 90.

As described above, the two assemblies 40 and 70 are placed over the shopping cart rail 5 in the provided space 130 to be sanitized and locked in place by snapping them together. The weight 150 allows the unit to remain in upright fashion while allowing the unit not to interfere with the nesting of the carts. The removal tool 160 is used to release the top cap 15, enabling easy replacement of the disposable sanitizer spray unit 30.

To use the sanitizer 10, the consumer squeezes the sanitizer pump dispensing sanitizer fluid 110 out of sanitizer spray outlet 120 while moving the complete assembly 10 along the shopping cart rail 5 or other handles. The contact of the slide fabric liner 60 with the rail in concert with the sanitizing spray will scrub and disinfect the shopping cart rail or other handles with a left and right motion along the rail.

As described and presented in the claims of the present disclosure, the invention, in accordance with preferred embodiments thereof is directed to a sanitizer for sliding over and sanitizing an elongated member such as a shopping cart handle includes a main body including a bottom housing and a top housing selectively interlockable with each other and defining therebetween a tunnel having a cross-sectional dimension and a general shape that match a corresponding cross sectional dimension and a shape of the elongated member. The top housing has a chamber for holding therein a sanitizing fluid dispenser that is positioned to dispense a sanitizing fluid onto the elongated member. A wiping material is disposed along the tunnel in the main body, in a position and in a manner that enables wiping the sanitizing fluid onto the elongated member as the sanitizer is slid over the elongated member.

Preferably, a weight is disposed in the bottom housing for orienting the sanitizer in an upright position on the elongated member. A cap is removeably mountable to the top housing to secure the sanitizing fluid dispenser thereto. The wiping material comprises a U-shaped bottom wiper that is covered by a top wiper. The top wiper and the bottom wiper are constructed of foam material for improved wiping of the sanitizing fluid onto the elongated member. The top housing includes a resting surface for an actuator of the sanitizing fluid dispenser. A removal tool may be included for unlocking the cap from the top housing.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A sanitizer for sliding over and sanitizing an elongated member, the sanitizer comprising:
   a main body including a bottom housing and a top housing selectively interlockable with each other and defining therebetween a tunnel having a cross-sectional dimension and a general shape that match a corresponding cross sectional dimension and a shape of the elongated member;
   the top housing having a chamber for holding therein a sanitizing fluid dispenser with a spray outlet that is positioned to dispense a sanitizing fluid onto the elongated member outside the main body; and
   a wiping material disposed along the tunnel in the main body, in a position and in a manner that enables wiping the sanitizing fluid onto the elongated member as the sanitizer is slid over the elongated member.

2. The sanitizer of claim 1, including a weight disposed in the bottom housing for orienting the sanitizer in an upright position on the elongated member.

3. The sanitizer of claim 2, including a retainer plate for the weight to hold it to a bottom surface of the bottom housing.

4. The sanitizer of claim 1, including a cap removeably mountable to the top housing to secure the sanitizing fluid dispenser thereto.

5. The sanitizer of claim 4, including top snap tabs configured to connect the cap to the top housing.

6. The sanitizer of claim 5, including a removal tool for unlocking the cap from the top housing.

7. The sanitizer of claim 1, the wiping material comprises a U-shaped bottom wiper that is covered by a top wiper.

8. The sanitizer of claim 7, wherein the top wiper and the bottom wiper are constructed of foam material for improved wiping of the sanitizing fluid onto the elongated member.

9. The sanitizer of claim 1, wherein the elongated member comprises a rail or a handle that visitors contact at public establishments.

10. The sanitizer of claim 9, wherein the rail or handle are on a shopping cart.

11. The sanitizer of claim 1, wherein the top housing includes a resting surface for an actuator of the sanitizing fluid dispenser.

12. The sanitizer of claim 1, including snap tab connectors to interlock the bottom housing with the top housing.

* * * * *